(12) United States Patent
Kleinwaechter et al.

(10) Patent No.: US 9,452,299 B2
(45) Date of Patent: Sep. 27, 2016

(54) FLEXIBLE APPLICATOR FOR RADIATION THERAPY

(71) Applicant: Carl Zeiss Meditec AG, Jena (DE)

(72) Inventors: Timo Kleinwaechter, Muensingen (DE); Volker Hausam, Singen (DE); Zoran Reiter, Emmingen (DE)

(73) Assignee: Carl Zeiss Meditec AG, Jena (DE)

( * ) Notice: Subject to any disclaimer, the term of this patent is extended or adjusted under 35 U.S.C. 154(b) by 343 days.

(21) Appl. No.: 14/278,312

(22) Filed: May 15, 2014

(65) Prior Publication Data

US 2014/0288350 A1    Sep. 25, 2014

Related U.S. Application Data

(63) Continuation of application No. PCT/EP2013/000349, filed on Feb. 6, 2013.

(30) Foreign Application Priority Data

Feb. 8, 2012  (DE) .................. 10 2012 002 466

(51) Int. Cl.
    *A61N 5/10*    (2006.01)
(52) U.S. Cl.
    CPC ........... *A61N 5/1014* (2013.01); *A61N 5/1042* (2013.01); *A61N 5/1081* (2013.01); *A61N 2005/1094* (2013.01)
(58) Field of Classification Search
    CPC ............. A61N 5/1014; A61N 5/1081; A61N 5/1042; A61N 5/1027; A61N 2005/1094

USPC ......................................................... 600/1–8
    See application file for complete search history.

(56) References Cited

U.S. PATENT DOCUMENTS

| 5,036,201 A | 7/1991 | Carroll et al. |
| 2008/0009659 A1* | 1/2008 | Smith .................. A61N 5/1015 600/3 |

FOREIGN PATENT DOCUMENTS

| DE | 44 13 491 | 8/1995 |
| WO | WO 2006/031771 | 3/2006 |

OTHER PUBLICATIONS

International Search Report for corresponding PCT Appl No. PCT/EP2013/000349, dated Apr. 3, 2013.

* cited by examiner

*Primary Examiner* — Christine H Matthews
*Assistant Examiner* — Kaylee Wilson
(74) *Attorney, Agent, or Firm* — Fish & Richardson P.C.

(57) ABSTRACT

An applicator for use in radiation therapy comprises:
  a main body for holding a radiation source, wherein the main body has a cavity extending along a main axis of the main body in the interior thereof; and
  an absorption body which is movably connected to the main body and influences the radiation emerging from the radiation source in such a way that a preferred radiation direction is defined,
wherein the absorption body is movable with respect to the main body in such a way that the preferred radiation direction can be tilted into a plurality of different positions relative to the main axis of the main body.

19 Claims, 4 Drawing Sheets

"unlock"

"lock"

"lock"

"lock"

FLEXIBLE APPLICATOR FOR RADIATION THERAPY

CROSS-REFERENCE TO RELATED APPLICATIONS

The present application is a continuation of, and claims benefit under 35 USC 120 to, international application PCT/EP2013/000349, filed Feb. 6, 2013, which claims benefit under 35 USC 119 of German Application No. 10 2012 002 466.5, filed Feb. 8, 2012. The entire disclosure of international application PCT/EP2013/000349 is incorporated by reference herein.

The present invention relates to an applicator for use in radiation therapy, comprising a main body for holding a radiation source in a cavity of the main body, and an absorption body which has an opening through which radiation can emerge. The size and the shape of the emergence opening of the absorption body in this case determine the emergence direction and the cross section of the emerging radiation.

TECHNICAL BACKGROUND

In intraoperative radiation therapy (IORT), it is often necessary to irradiate tissue which is not easily accessible. In the case of known applicators for irradiating a surface, it is only possible to irradiate tissue which can be reached from the outside in the direction of a main axis of the applicator. By way of example, when irradiating the pelvic bone, this leads to a large part of the intestines having to be moved to the side during the intervention in order to have access to the tissue to be irradiated. An angled applicator could be guided laterally past the intestines and irradiate the desired area on the pelvic bone. In this case, a different angle of the applicator for different applications is, however, ideal in each case.

In some radiation machines, a radiation source which radiates uniformly in all directions is used for intraoperative radiation therapy. However, in order to achieve desired radiation characteristics, it is conventional to selectively absorb some spatial directions of the emitted radiation such that a preferred radiation direction is defined.

It is an object of the present invention to provide an applicator for radiation therapy in which the preferred radiation direction can be adjusted relative to a main axis of the applicator, and which is simple to clean.

This object is achieved by an applicator for use in radiation therapy which comprises: a substantially cylindrically embodied main body for holding a radiation source, wherein the main body has a cavity extending along a main axis of the main body in the interior thereof; and a substantially cylindrically embodied absorption body which is movably connected to the main body and which influences the radiation emerging from the radiation source in such a way that a preferred radiation direction is defined, wherein the main body and the absorption body are arranged in succession in the longitudinal direction and the plane in which the ends of the two cylinders abut against one another is angled relative to the main axis of the main body, wherein the absorption body is rotatably connected to the main body and the axis of rotation of the absorption body is angled with respect to the main axis of the main body such that the preferred radiation direction can be tilted into a plurality of different positions relative to the main axis of the main body. Further advantageous embodiments are specified in the disclosure.

An applicator according to the invention for use in radiation therapy comprises:
a main body for holding a radiation source, wherein the main body has a cavity extending along a main axis of the main body in the interior thereof; and
an absorption body which is movably connected to the main body and which influences the radiation emerging from the radiation source in such a way that a preferred radiation direction is defined,
wherein the absorption body is movable with respect to the main body in such a way that the preferred radiation direction can be tilted into a plurality of different positions relative to the main axis of the main body.

Such an applicator enables the irradiation of tissue which is not easily accessible for conventional applicators because it cannot be reached in a straight line from the outside. In the applicator according to the invention, the emergence direction of the radiation can be tilted relative to the main axis of the main body of the applicator in such a way that it is also possible to reach tissue which does not lie perpendicular to a main axis of the applicator.

The absorption body is preferably detachably connected to the main body in order to enable simple cleaning and sterilization of the applicator.

In accordance with one embodiment of the applicator according to the invention, the absorption body is rotatably connected to the main body, wherein the axis of rotation of the absorption body is angled with respect to the main axis of the main body. This renders it possible to change the emergence direction of the radiation by rotating the absorption body relative to the main body.

Furthermore, a locking mechanism can be provided for locking the position of the absorption body relative to the main body. In accordance with one embodiment of the present invention, the locking mechanism comprises a retaining ring which enables reliable locking of the absorption body in a structurally simple manner.

Here, the absorption body can be lockable into a plurality of different positions relative to the main body, wherein the emergence direction of the radiation relative to the main axis of the main body assumes a different value for each position. Thus, an applicator is provided, in which the emergence direction of the radiation can be set in a plurality of different directions relative to the main axis of the main body and can in each case be locked in the relevant direction.

In accordance with another embodiment, the absorption body can be continuously movable relative to the main body and can be lockable in any position by the locking mechanism. As a result of this, it is possible, within a predefined movement range of the absorption body, to set any angle of the emergence direction of the radiation relative to the direction of the main axis of the main body.

The absorption body can comprise an absorption mechanism holder and an absorption mechanism, wherein the absorption mechanism is embodied in such a way that it influences beam characteristics, such as diameter, intensity and propagation direction, of the emerging radiation. By way of example, the absorption mechanism can be configured as a stop in order to define a diameter of the emerging radiation, or the absorption mechanism can define beam characteristics, such as the penetration depth into the tissue to be irradiated.

Here, the absorption mechanism can comprise any component which, for example due to the spatial distribution of its density and/or its material strength, is able to influence the radiation produced by the radiation source.

This two-part setup of the absorption body is advantageous since shape and material of the absorption mechanism holder can be optimized in view of the movement and locking of the absorption body, and the desired absorption characteristics for the utilized radiation can be realized independently of these considerations by suitable selection of the absorption mechanism.

Furthermore, the present invention comprises an applicator system for use in radiation therapy, comprising the applicator described above and a plurality of absorption bodies, which can each be connected to the main body of the applicator and which each influence the radiation emerging from the radiation source in such a way that a preferred radiation direction and in each case different beam characteristics of the emerging radiation are defined. Such an applicator system therefore enables not only the irradiation of tissue with different angles relative to the main axis of the applicator but also simple setting of different desired radiation cross sections and radiation characteristics.

In the following text, some embodiments of the present invention will be explained in an exemplary manner on the basis of the attached drawings. In detail:

Figure 1:
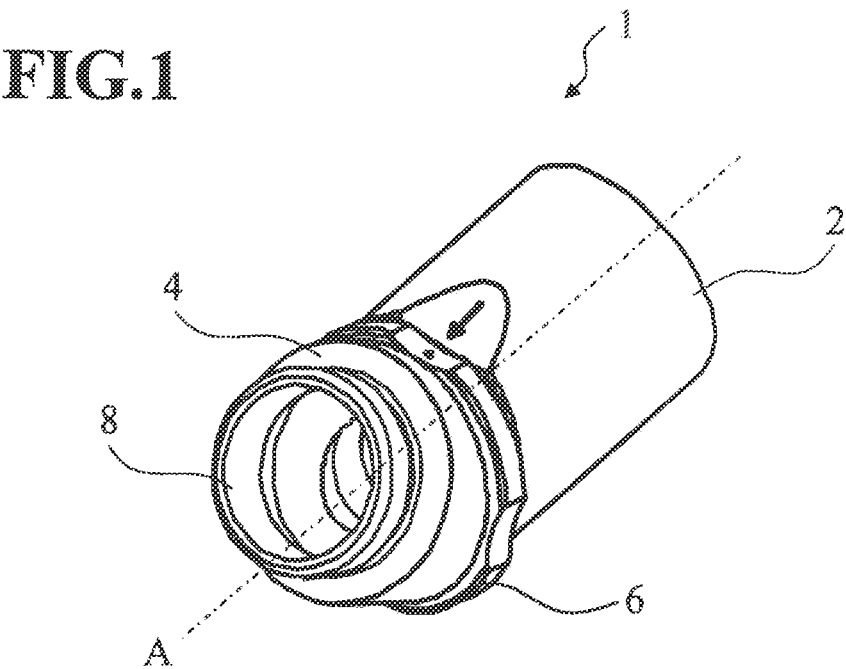
FIG. 1 shows a view of an applicator in accordance with one embodiment of the present invention.

As shown in FIG. 1, an applicator 1 according to the invention comprises a main body 2, an absorption body 4 rotatably fastened to the main body 2 and a retaining ring 6.

In its interior, the cylindrical main body 2 has a cavity into which a radiation source (not shown) can be inserted. Here, the radiation source can comprise any radiation source suitable for use in intraoperative radiation therapy. In some radiation machines for IORT, the radiation source is attached in an end region of the applicator 1 such that the radiation source can be brought as close as possible to the tissue to be irradiated during the therapy.

The absorption body 4 is formed from a material which absorbs the radiation emerging from the radiation source. Here, shape and material of the absorption body 4 are configured such that the radiation emerging from the radiation source in a spherical manner is selectively absorbed such that radiation substantially only emerges from the absorption body 4 in a preferred radiation direction. To this end, an exemplary embodiment of an absorption body 4 can have an emergence opening 8 at its end, through which opening the radiation can emerge. In this case, the direction of the emerging radiation relative to a main axis A of the main body 2 is defined by the position and alignment of the emergence opening 8 relative to the main axis A of the main body 2.

An absorption mechanism (not shown) can be inserted into the emergence opening 8; it is configured in such a way that the beam characteristics of the emerging radiation can be set in accordance with the desired application, for example in accordance with the desired penetration depth into the tissue to be irradiated. In this context, an absorption mechanism is understood to mean any component which is suitable for influencing beam characteristics such as the beam shape and strength. Alternatively, an absorption mechanism in the form of a stop is also feasible, or it is feasible to use the radiation emerging from the emergence opening 8 for irradiating the tissue, without influencing the radiation further.

As shown in FIGS. 2a to 2d, the absorption body 4 is rotatable about an axis of rotation D, which is tilted by an angle α with respect to the main axis A of the main body 2. In the shown embodiment, the angle α is 20°, and so maximum angling of 40° of the emergence direction of the radiation with respect to the main axis A of the main body 2 is achieved (see FIG. 2a). Other values for α, and therefore for the maximum value of the angling of the emergence direction of the radiation with respect to the main axis A of the main body, are also feasible.

Figure 2A:
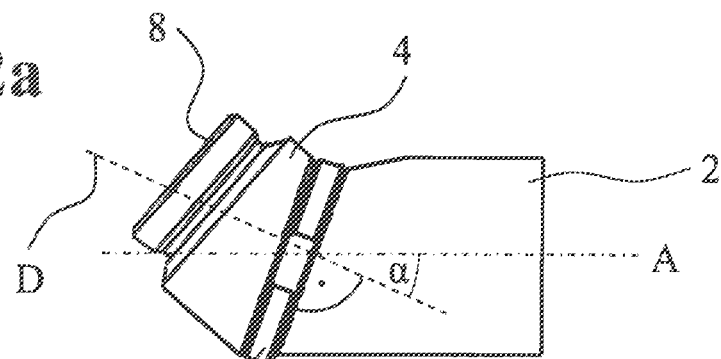
FIGS. 2a-2d show different positions of the absorption body of the applicator shown in FIG. 1.
Figure 2B:
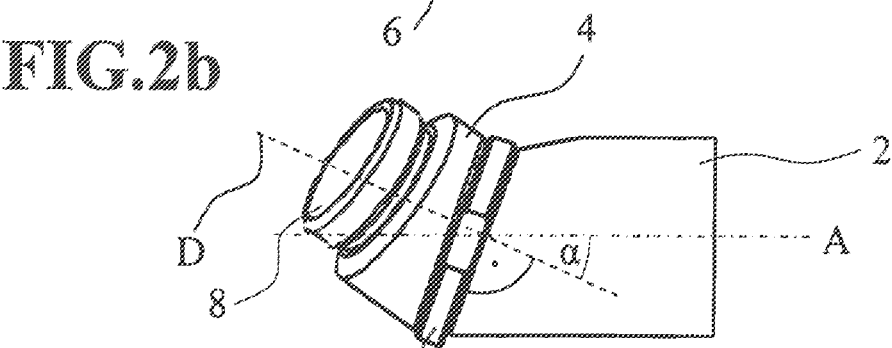
Figure 2C:
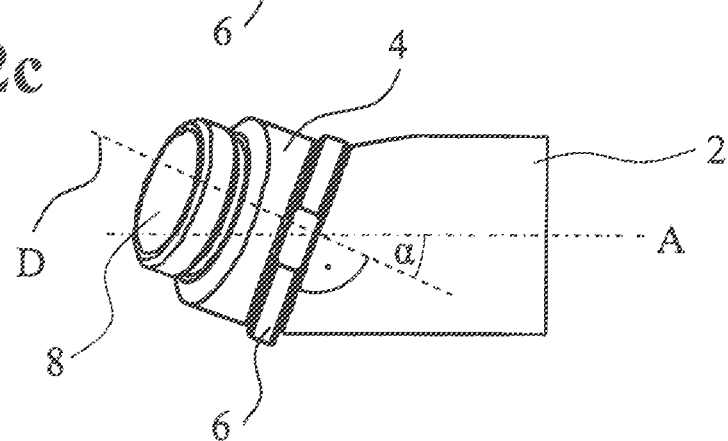
Figure 2D:
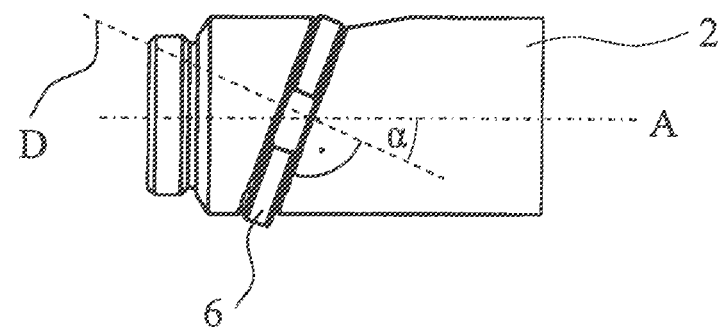

As can be seen from FIG. 2d, in the present invention, the rotation of the absorption body 4 about an axis of rotation D, which is tilted relative to the main axis A of the main body 2, is implemented in a structurally particularly simple manner by virtue of main body 2 and absorption body 4 each being embodied substantially cylindrically, with the two cylinders being arranged in succession in the longitudinal direction. The plane in which the ends of the two cylinders abut against one another is angled relative to the main axis A of the main body 2. This renders it possible in a simple manner to realize a pivot joint, which enables pivoting of the emergence opening 8 of the radiation with respect to the main axis A of the main body and which merely has a gap, which is simple to clean and easily accessible, between the main body 2 and the absorption body 4, into which gap blood or contaminants can penetrate during use.

As shown in FIGS. 2a to 2d, a rotation of the absorption body 4 relative to the main body 2 brings about a change in the angle of the emergence direction of the radiation with respect to the main axis A of the main body. In this case, the maximum and minimum possible values for the movement range of the emergence direction of the radiation with respect to the main axis A of the main body are shown in FIGS. 2a and 2d.

Figure 3:
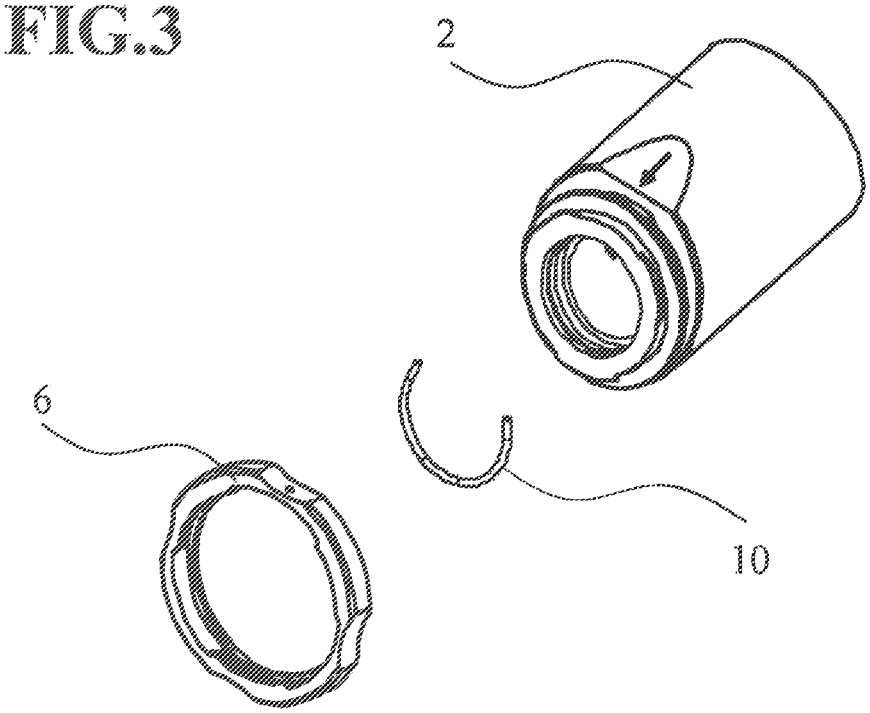
FIG. 3 shows the main body, a retaining ring and an associated split washer.

As can be seen from FIG. 3, the retaining ring 6 and a split washer 10 are provided for fastening the absorption body 4 on the main body 2.

Figure 4:
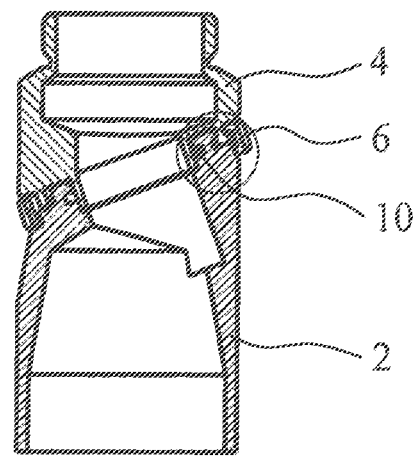
FIG. 4 shows a cross section through the applicator shown in FIG. 2d.
Figure 5:
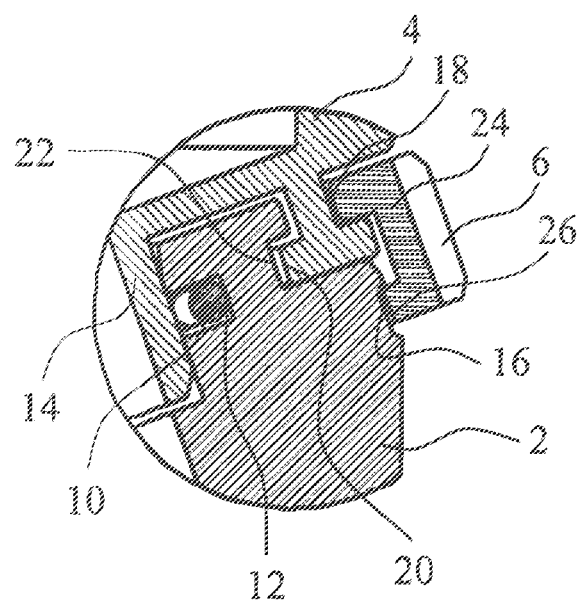
FIG. 5 shows a detailed view of the cross section shown in FIG. 4.

The interaction between retaining ring 6 and split washer 10 is depicted in FIGS. 4 and 5. The split washer 10 lies in a groove 12 in the inner surface of the main body 2. A bearing surface 14 of the absorption body 4 is in contact with the split washer 10 in such a way that the friction between the split washer 10 and the bearing surface 14 prevents unwanted rotation of the absorption body 4 relative to the main body 2.

With appropriate protrusions 24, 26, the retaining ring 6 engages into grooves 16, 18 on the respective outer surfaces of the main body 2 and of the absorption body 4. Furthermore, for additional axial retention of the absorption body 4 relative to the main body 2, a projection 20 of the absorption body 4 engages into a groove 22 on the outer surface of the main body 2.

Here, the appropriate grooves and projections are in each case not provided on the whole circumference of the main body 2, of the retaining ring 6 and of the absorption body 4. Thickenings and clearances of the groove 16 of the main body 2 and of the protrusion 26 of the retaining ring 6 alternate in such a way that, by a rotation of the retaining ring 6, as shown in FIGS. 6b to 6d, the retaining ring 6 axially retains the absorption body 4 on the main body 2 in the positions denoted by "lock", while a rotation of the absorption body 4 relative to the main body 2 is still possible.

Figure 6A:
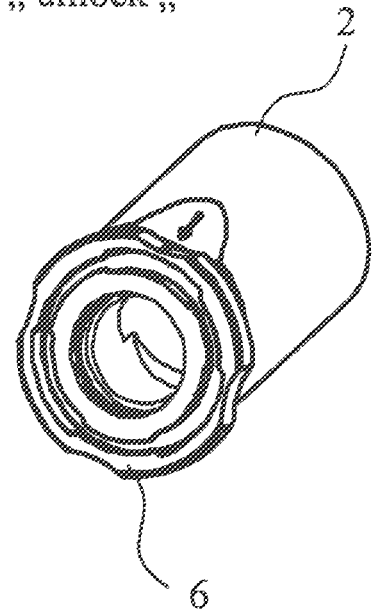
FIGS. 6a-6d show different positions of the retaining ring on the applicator main body.
Figure 6B:
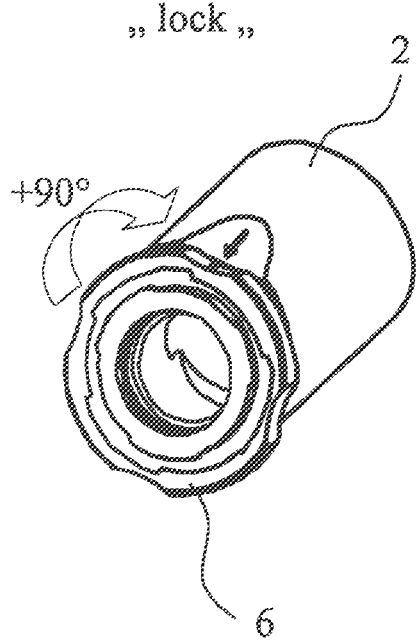
Figure 6C:
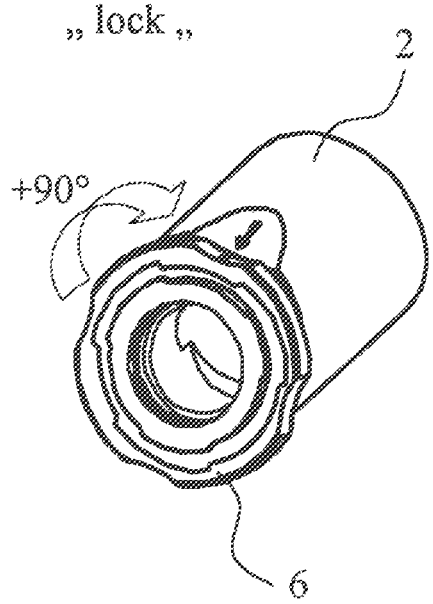
Figure 6D:
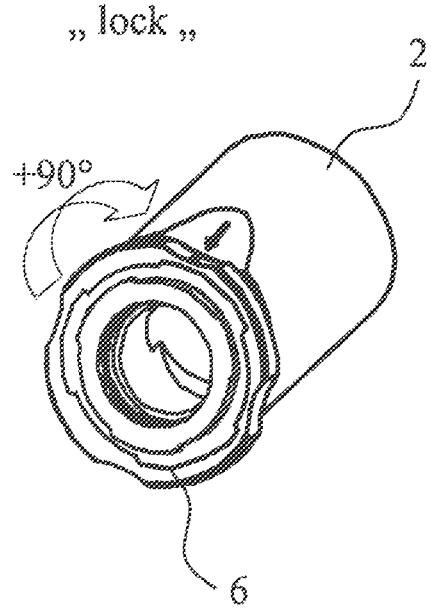

In the release position of the retaining ring 6, which is shown in FIG. 6a and denoted by "unlock", the absorption body 4 can be removed from the main body 2 in the axial direction. However, to this end, the absorption body 4 has to be rotated relative to the main body 2 in such a way that the engagement between the respective grooves and projections of the absorption body 4 and of the main body 2 is also lifted.

Thus, the retaining ring 6 enables simple assembly and disassembly of the absorption body 4 relative to the main body 2. This is advantageous, in particular in view of cleaning the pivot joint between main body 2 and absorption body 4. In accordance with a development of the present embodiment, different absorption bodies 4 can be provided, wherein the emergence openings in each case have different dimensions and configurations in order, in each case, to provide different beam characteristics of the emerging radiation. A user can then assemble the appropriate absorption body 4 for each application, without in each case having to replace the complete applicator 1.

By an appropriate configuration of the groove 18 on the absorption body 4 and of the protrusion 24 on the retaining ring 6, it is furthermore possible to detach the retaining ring 6 from the absorption body 4 for cleaning purposes.

Here, the engagement between the main body 2 and the retaining ring 6 can be configured in such a way that the retaining ring 6 can be rotated, in each case latching, by 90° with respect to the main body such that the user can easily set the respective locking and release positions of the retaining ring 6. By way of example, two thickenings in the snap groove 16 of the main body 2 and four clearances in the protrusion 26 of the retaining ring 6 are provided to this end.

The applicator 1 shown in the present embodiment allows a continuous adjustment of the angle of the emergence opening 8 with respect to the main axis A of the main body in an angular range between 0 and 40°. However, it is also feasible, for example via a latching mechanism with a suitable configuration, to provide a plurality of discrete positions of the absorption body 4 relative to the main body 2. Such an adjustment mechanism with a plurality of defined positions of the absorption body 4 relative to the main body 2 allows a user to in each case set a number of specified, predetermined angles precisely.

LIST OF REFERENCE SIGNS

1 Applicator
2 Main body
4 Absorption body
6 Retaining ring
8 Emergence opening
10 Split washer
12 Groove
14 Bearing surface
16 Groove
18 Groove
20 Projection
22 Groove
24 Protrusion
26 Protrusion
A Main axis of the main body
D Axis of rotation of the absorption body
α Angle between A and D

The invention claimed is:

1. An applicator, comprising:
a substantially cylindrical main body configured to hold a radiation source, an interior of the main body having a cavity which extends along a main axis of the main body;
a substantially cylindrical absorption body movably connected to the main body; and
a pivot joint configured to enable an axis of rotation of the absorption body, wherein:
the absorption body is configured so that, when the main body is holding the radiation source and the radiation source is emitting radiation, the absorption body influences the radiation to define a preferred radiation direction;
the main body and the absorption body are arranged in succession in a longitudinal direction;
in a plane, an end of the cylindrical main body abuts against an end of the absorption body;
the plane is angled relative to the main axis of the main body;
the absorption body is rotatably connected to the main body;
the axis of rotation of the absorption body is angled with respect to the main axis of the main body so that the preferred radiation direction is tiltable into a plurality of different positions relative to the main axis of the main body.

2. The applicator of claim 1, wherein the absorption body is detachably connected to the main body.

3. The applicator of claim 2, further comprising a locking mechanism configured to lock a position of the absorption body with respect to the main body.

4. The applicator of claim 3, wherein the locking mechanism comprises a retaining ring.

5. The applicator of claim 4, wherein:
the absorption body is lockable in a plurality of different positions relative to the main body; and
relative to the main axis of the main body, the preferred radiation direction is different for each position.

6. The applicator of claim 5, wherein the absorption body is continuously movable relative to the main body, and the absorption body is lockable in any position via the locking mechanism.

7. The applicator of claim 6, wherein:
the absorption body comprises an absorption mechanism and a holder configured to hold the absorption mechanism; and
the absorption mechanism is configured to influence beam characteristics of the emitted radiation.

8. The applicator of claim 3, wherein:
the absorption body is lockable in a plurality of different positions relative to the main body; and
relative to the main axis of the main body, the preferred radiation direction is different for each position.

9. The applicator of claim 8, wherein the absorption body is continuously movable relative to the main body, and the absorption body is lockable in any position via the locking mechanism.

10. The applicator of claim 9, wherein:
the absorption body comprises an absorption mechanism and a holder configured to hold the absorption mechanism; and
the absorption mechanism is configured to influence beam characteristics of the emitted radiation.

11. The applicator of claim 3, wherein the absorption body is continuously movable relative to the main body, and the absorption body is lockable in any position via the locking mechanism.

12. The applicator of claim 11, wherein:
- the absorption body comprises an absorption mechanism and a holder configured to hold the absorption mechanism; and
- the absorption mechanism is configured to influence beam characteristics of the emitted radiation.

13. The applicator of claim 2, wherein:
- the absorption body is lockable in a plurality of different positions relative to the main body; and
- relative to the main axis of the main body, the preferred radiation direction is different for each position.

14. The applicator of claim 2, wherein the absorption body is continuously movable relative to the main body, and the absorption body is lockable in any position via a locking mechanism.

15. The applicator of claim 14, wherein:
- the absorption body comprises an absorption mechanism and a holder configured to hold the absorption mechanism; and
- the absorption mechanism is configured to influence beam characteristics of the emitted radiation.

16. The applicator of claim 1, further comprising a locking mechanism configured to lock a position of the absorption body with respect to the main body.

17. The applicator of claim 16, wherein the locking mechanism comprises a retaining ring.

18. The applicator of claim 1, wherein:
- the absorption body comprises an absorption mechanism and a holder configured to hold the absorption mechanism; and
- the absorption mechanism is configured to influence beam characteristics of the emitted radiation.

19. The applicator of claim 18, wherein the beam characteristics are selected from the group consisting of beam diameter, beam intensity and beam propagation direction.

* * * * *